(12) United States Patent
Tong et al.

(10) Patent No.: US 8,128,932 B2
(45) Date of Patent: Mar. 6, 2012

(54) ANTI-VEGFR MONOCLONAL ANTIBODY, METHOD OF MAKING AND USES THEREOF

(75) Inventors: Jie Tong, Oakland, CA (US); Jian Min Fang, Shanghai (CN); Wenqing Wu, Shanghai (CN); Bin Zhang, Shanghai (CN); Desheng Jiang, Shanghai (CN)

(73) Assignee: Shanghai Aosaiersi Biotech Co., Ltd., Shanghai (CN)

( * ) Notice: Subject to any disclaimer, the term of this patent is extended or adjusted under 35 U.S.C. 154(b) by 11 days.

(21) Appl. No.: 12/542,239

(22) Filed: Aug. 17, 2009

(65) Prior Publication Data

US 2011/0038874 A1 Feb. 17, 2011

(51) Int. Cl.
*A61K 39/395* (2006.01)
*A61K 39/00* (2006.01)
*C07K 16/00* (2006.01)
*C07K 16/28* (2006.01)

(52) U.S. Cl. ............ 424/141.1; 424/142.1; 424/143.1; 530/388.1; 530/388.2; 530/388.22

(58) Field of Classification Search .................. None
See application file for complete search history.

(56) References Cited

U.S. PATENT DOCUMENTS 7,084,257 B2 * 8/2006 Deshpande et al. ....... 530/387.9

FOREIGN PATENT DOCUMENTS

| CN | 2007-101717628 | 9/2008 |
| WO | WO 00/44777 | 8/2000 |
| WO | WO 2003085089 | * 10/2003 |

OTHER PUBLICATIONS

Rudikoff et al, Proc. Natl. Acad. Sci. USA 1982 vol. 79 p. 1979-1983.*
Henry et al, Cancer Res. 64: 7995-8001, Nov 1, 2004.*
Stancoviski et al, Proceedings of the National Academy of Science USA 88: 8691-8695, 1991.*
Riemer et al, Mol. Immunol. 42: 1121-1124, 2005.*
Rudikoff et al, Proc Natl Acad Sci USA 79:1979, 1982.*
Piatesi et al, ChemBio Chem 5: 460-466, 2004.*
Wu et al, J. Mol. Biol. 294:151-162, 1999.*

* cited by examiner

*Primary Examiner* — Phuong Huynh
(74) *Attorney, Agent, or Firm* — Saliwanchik, Lloyd & Eisenschenk

(57) ABSTRACT

The subject invention is directed to a VEGFR2 (vascular endothelial growth factor receptor II) monoclonal antibody (mAb), and the amino acid sequence of the heavy chain and the light chain of the mAb. The invention is also directed to methods for making the VEGFR2 mAb, and methods of using the mAb to inhibit angiogenesis and treat various conditions such as tumor and retinal diseases.

6 Claims, No Drawings

ANTI-VEGFR MONOCLONAL ANTIBODY, METHOD OF MAKING AND USES THEREOF

FIELD OF TECHNOLOGY

The subject invention pertains to biotechnology. In particular, the invention pertains to a monoclonal antibody and its use in therapy.

BACKGROUND

Angiogenesis is a process involving the growth of new blood vessels from pre-existing vessels. In healthy adults, angiogenesis is quiescent in most of the organs, and is only present in limited circumstances such as the menstrual cycle. However, angiogenesis may occur in certain pathological conditions, such as during tumor growth, retinal disorders and wound healing. Studies have shown that angiogenesis plays an important role in the progression of tumors and development of retinal diseases. Inhibiting angiogenesis can be an effective treatment of many types of cancer. (Folkman, 2002, Role of Angiogenesis in Tumor Growth and Metastasis, Semin Oncol. 29 (6 Suppl 16): 15-8; Witmer et al., 2003, Vascular Endothelial Growth Factors and Angiogenesis in Eye Diseases, Prog Retin Eye Res. 22:1-29).

Angiogenesis is regulated by many factors. The vascular endothelial cell growth factor (VEGF) plays a critical role in angiogenesis (Leung et al., 1989, Vascular Endothelial Growth Factor Is a Secreted Angiogenic Mitogen, Science, 246: 1306-1309; Ferrara et al., 2003, The Biology of VEGF and Its Receptors, Nature Medicine 9: 669-676). VEGF is a polypeptide, secreted by multiple types of cells, and it is highly expressed in tumor cells. High levels of VEGF expression correlate to aggressiveness of tumors.

VEGF binds to specific receptors in the vascular endothelial cells, and initiates a series of signal transduction pathways that lead to the proliferation and migration of vascular endothelial cells. VEGF binds to two different receptors, that is, VEGFR1 and VEGFR2. VEGFR2 is the key receptor for VEGF signal transduction that triggers angiogenesis. (Neufeld et al., 1999, Vascular Endothelial Growth Factor (VEGF) and its Receptors, The FASEB Journal, 13:9-22).

VEGFR2 consists of the extracellular domain, the transmembrane domain and the intracellular domain. VEGF binds to the extracellular domain of VEGFR2. The binding leads to the autophosphoration of tyrosine kinase in the intracellular domain, which as a result initiates signal transduction, resulting in vascular endothelial cell proliferation, migration, and vessel formation. In addition, VEGFR2-mediated signal transduction inhibits the apoptosis of vascular endothelial cells.

Given the key role of VEGFR2 in the signal transduction for angiogenesis, it is possible to inhibit angiogenesis, thus treat diseases, by blocking the binding of VEGF to VEGFR2. Therefore, pharmaceutical agents blocking the VEGFR2 pathway are capable of treating many angiogenesis-related diseases, such as cancers and AMD.

Monoclonal antibodies (mAb) have become a new class of therapeutic agent due to their ability to bind with high specificity to a target, their long plasma half-life, and their low toxicity/side effects. Furthermore, recent progress in humanized or full human antibody technologies have helped to avoid the early problems associated with murine antibodies, including immunogenicity in vivo. Therefore, monoclonal antibodies have become an attractive option for pharmaceutical compositions.

The human body has millions of lymphocytes, secreting various antibodies. Each lymphocyte secretes only one type of mAb specific to a single epitope. Therefore, each human has a huge number of mAbs. Antibodies that are secreted in different persons may vary due to various antigens exposed to the individuals. In some persons, in response to specific physiological and pathological conditions, antibodies that bind to the person's own proteins are produced.

Human mAbs can be generated by isolating lymphocytes secreting specific antibodies. In addition, human mAbs can also be generated by other methods, such as by screening human antibody phage-display library or immunizing transgenic mice that carry human antibody genes.

Chinese Patent No. 00805856.3 discloses a human immunoglobulin molecule, including its amino acid sequences, which binds to and neutralizes VEGFR2. Currently, no mAb containing the amino acid sequence identical or similar to the subject invention has been disclosed for the inhibition of angiogenesis and the treatment of vascular diseases.

BRIEF SUMMARY

The subject invention provides monoclonal antibodies that specifically bind to VEGF receptors.

The subject invention also provides nucleic acids comprising nucleotide sequences encoding such antibodies; vectors comprising such nucleic acids; host cells and organisms comprising such nucleic acids and/or vectors; and compositions, such as pharmaceutically acceptable compositions and kits, comprising such proteins, nucleic acids, vectors, and/or cells and typically one or more additional ingredients that can be active ingredients or inactive ingredients that promote formulation, delivery, stability, or other characteristics of the composition (e.g., various carriers).

The invention further provides various new and useful methods for making and using such antibodies, nucleic acids, vectors, cells, organisms, and/or compositions, such as in the modulation of VEGF-mediated biological activities, for example in the treatment of diseases related thereto.

Advantageously, the antibodies of the present invention can be used to block VEGF from binding to VEGFR2. Thus, the antibodies can be used to inhibit vascular endothelial cell proliferation.

In one embodiment, the antibodies can be used to block angiogenesis, including treating angiogenesis-related disorders. Such disorders include, but are not limited to, cancer, retinopathy, and age-related macular degeneration.

Advantageously, the novel materials and methods provided here for blocking binding at the novel VEGFR2 receptor overcome shortfalls of current angiogenesis inhibitor drugs.

BRIEF DESCRIPTION OF THE SEQUENCES

SEQ ID NO:1 is an amino acid sequence for the immunoglobulin heavy chain of an antibody of the subject invention.

SEQ ID NO:2 is an amino acid sequence for the immunoglobulin light chain of an antibody of the subject invention.

SEQ ID NO:3 is a primer useful according to the subject invention.

SEQ ID NO:4 is a primer useful according to the subject invention.

DETAILED DISCLOSURE OF THE INVENTION

One embodiment of the subject invention provides a VEGFR2 mAb, in which the amino acid sequence of the immunoglobulin heavy chain is SEQ ID No:1 and the amino acid sequence of the immunoglobulin light chain is SEQ ID NO:2. Also contemplated are antibodies having amino acid sequences containing one or more amino acid additions, substitutions, insertions or deletions. These variant antibodies include, for example, allelic variants of the exemplified antibody.

A second embodiment provides a DNA sequence encoding the VEGFR2 mAb. In a specific embodiment, the DNA sequence is a cDNA.

A third embodiment provides vectors that carry a DNA sequence encoding the mAb. The vector can be, for example, a plasmid or virus.

A fourth embodiment provides a host cell containing DNA encoding the VEGFR2 mAb.

A fifth embodiment provides a method for making the VEGFR2 mAb, comprising:

1) transplanting human lymphocytes into mice with immune-deficiency and immunizing the mice with VEGFR2;

2) fusing the spleen lymphocytes produced according to step 1 with mouse myeloma to generate hybridomas; and 3) screening hybridoma cell lines by identifying hybridoma clones that secrete mAbs that specifically bind to VEGFR2;

or, comprising:

1) synthesizing cDNAs by reverse-transcribing RNA of the hybridoma cells that secrete the anti-VEGFR2 antibody;

2) amplifying the DNA of heavy chains and the light chains of the VEGFR2 antibodies by, for example, PCR, using the cDNA of the step 1) as a template;

3) inserting the DNA amplified by step 2 into a mammalian-expressing plasmid; and 4) purifying the plasmid of step 3), and transfecting CHO cells with the purified plasmid to produce recombinant antibodies;

or, comprising:

1) inserting the cDNA of step 3) into a plasmid containing dehydrofolate reductase (DHFR) in such way that the light chain and the heavy chain of the cDNA are in the same plasmid, wherein the cDNA (expression) of the light chain and the heavy chain are driven by an independent CMV promoter, and wherein the DHFR gene expression is driven by a SV40 promoter;

2) isolating the plasmid of step (1) and transfecting the plasmid into human CHO cells with DHFR deficiency;

3) culturing the CHO cells of step 2) and selecting the cell lines having the highest protein expression; and 4) applying MTX-pressure to the cell lines obtained by step 3), increasing MTX-pressure, and selecting the cloned cells exhibiting the highest level of antibody protein expression.

A sixth embodiment provides a composition for inhibiting angiogenesis, comprising the mAb of the subject invention having a concentration effective for treatment and a pharmaceutically acceptable carrier. Specifically, the effective concentration of the composition can be, for example, 0.1-100 mg per kg of body weight for intravenous injections or 0.01-100 mg per eye for intravitreous injection.

A seventh embodiment provides a method for neutralizing VEGFR2, including applying the mAh of the subject invention with an effective concentration to mammalian cells so that the mAbs block VEGFR2.

An eighth embodiment provides a method for inhibiting tumor growth or retinal neovascularization by administering the mAb at an effective concentration to mammalian cells so that the mAbs block VEGFR2.

This invention also provides methods that can be used to determine the biological activity of this antibody.

The antibodies of the subject invention, including antibody fragments, can be used to purify VEGF receptors. In a further embodiment antibodies can be produced that bind to the anti-VEGFR2 antibody described herein.

In order to generate a fully human anti-VEGFR antibody, a large number of human serum samples were screened by ELISA and a sample that was positive for anti-VEGFR2 antibodies was identified. The peripheral blood mononuclear cells from this patient were transplanted into immune-deficient mice and anti-VEGFR2 immune response was further boosted by immunizing the mice with VEGFR2 protein. The lymphocytes from these mice were fused to mouse myeloma cells to generate hybridomas that produce monoclonal antibodies. By this method, a number of hybridoma clones were isolated that secrete anti-VEGFR2 antibodies. Subsequently, a fully human monoclonal anti-VEGFR2 antibody was identified that blocks VEGFR2 from being bound by VEGF.

The subject invention provides amino acid sequences for the anti-VEGFR2 antibody. The amino acid sequence of the heavy chain of this monoclonal antibody is as shown in SEQ ID NO: 1. The amino acid sequence of the light chain of this monoclonal antibody is as shown in SEQ ID NO:2.

The DNA sequences of the heavy and light chains of this antibody were obtained by PCR using cDNA that had been reverse-transcribed from the RNA of antibody hybridoma as templates.

As is well known in the art, individual amino acids can be encoded by different DNA sequences. Hence, the amino acid sequences of this antibody can be encoded by different DNA sequences; these DNA sequences fall within the scope of the present invention.

Furthermore, based on the common knowledge of antibody structure, some amino acids in an antibody may be substituted, deleted, or added, without detracting the biological activities of the antibody. In some cases, changes in the amino acid sequence of an antibody may even improve the biological activities and/or improve certain properties compared to the original antibody. Therefore, it is possible to modify the amino acid sequences of this anti-VEGFR2 antibody to obtain antibody variants with similar, or even improved, biochemical or biological properties. These modified antibodies are within the scope of the present invention.

Production of the Antibody

After obtaining DNA sequences of this antibody, it became possible to produce these monoclonal antibodies by recombinant techniques. The DNA sequences encoding the antibody heavy and light chains can be inserted into a suitable vector. Specifically exemplified herein is the use of a plasmid as a vector. However, other vectors, such as viruses and DNA fragments, can also be used to express or produce this monoclonal antibody.

In the vector, the antibody open reading frames are located downstream of a promoter. A promoter drives transcription of mRNA from the antibody open reading frames that include a start codon and a stop codon. The antibody heavy chain and light chain open reading frames can be constructed within a single vector, but they can also be inserted into to two independent vectors.

The vector that encodes antibody DNA sequences can be introduced into host cells, which then express the recombinant antibody. Various types of cells can be used as host cells. However, because antibodies contain amino acid residues requiring glycosylation, mammalian cells are the ideal host cells because they provide glycosylation similar to the native antibodies. Among the most commonly used mammalian cells are Chinese hamster ovary (CHO) cells, mouse myeloma, HEK293 cells, etc. In addition, many other mammalian cells can also be used to express this antibody and are also included in this invention as host cells for the production of this antibody.

Furthermore, non-mammalian cells may also be used to express or produce the antibody invention. The non-mammalian cells may be eukaryotic cells, including but not limited to plant cells, insect cells, and yeast cells. The non-mammalian cells may also be prokaryotic cells, including but not limited to bacteria and fungi.

The methods that introduce the vector encoding the antibody sequences into host cells include those widely used in molecular biology. For plasmid transfection, the most commonly used methods are electroporation and liposome-based transfection. Electroporation is specifically exemplified herein but other methods can also be used for the same purpose.

In addition to the preferred cell culture approach, other methods can also be used to produce the antibody of the subject invention. For example, as it is well-known in the art, the antibody may be expressed in the organs of transgenic animals, such as in animal mammalian glands, muscles, or eggs. Moreover, the antibody can also be expressed in the organs of transgenic plants, such the leaves of a transgenic plant, etc.

The subject invention also provides an initial step for the purification of this monoclonal antibody from cell culture supernatants. The purified recombinant antibody can be properly formulated to become a monoclonal antibody drug.

Antibody Variations

An antibody that is contemplated for use in the present invention can be in any of a variety of forms, including a whole immunoglobulin, an antibody fragment such as Fv, Fab, and similar fragments, as well as a single chain antibody that includes the variable domain complementarity determining regions (CDR), and similar forms, all of which fall under the broad term "antibody," as used herein.

The term "human antibody," as used herein, is intended to include antibodies having variable and constant regions identical to, essentially identical to, or derived from human germline immunoglobulin sequences. Such human antibodies can include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences.

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment of an antibody yields an F(ab')$_2$ fragment that has two antigen binding fragments, which are capable of cross-linking antigen, and a residual other fragment (which is termed pFc'). Additional fragments can include diabodies, linear antibodies, single-chain antibody molecules, and multispecific antibodies formed from antibody fragments. As used herein, "antigen binding fragment" with respect to antibodies, refers to, for example, Fv, F(ab) and F(ab')$_2$ fragments. Of particular importance for binding are the first 110 to 130 amino acids at the N-terminus of the amino acid sequences exemplified herein. Thus, high identity in the N-terminus 110, 115, 120, 125, or 130 amino acids constituting the variable region is preferred. Variant sequences preferably have more than 75%, 90%, or even 95% identity in this region.

The subject invention further comprises fusion constructs wherein the antibody, or fragment thereof, may be fused to one or more additional entities. The additional entity(ies) may be for example linkers, toxins, carriers, solid supports, and/or detectable molecules. In this context the binding portion may consist or consist essentially of the antibody. By "consists essentially" it is meant that no other entity is present that substantially effects the ability of the antibody (or fragment thereof) to bind to VEGFR2.

"Specific binding" or "specificity" refers to the ability of an antibody or other agent to detectably bind an epitope presented on an antigen, such as a VEGFR2, while having relatively little detectable reactivity with other proteins or structures. Specificity can be relatively determined by binding or competitive binding assays, using, e.g., Biacore instruments. Specificity can be exhibited by, e.g., an about 10:1, about 20:1, about 50:1, about 100:1, 10.000:1 or greater ratio of affinity/avidity in binding to the specific antigen versus non-specific binding to other irrelevant molecules.

"Selectivity" refers to the preferential binding of a protein to a particular region, target, or peptide as opposed to one or more other biological molecules, structures, cells, tissues, etc. For example, selectivity can be determined by competitive ELISA or Biacore assays. The difference in affinity/avidity that marks selectivity can be any detectable preference (e.g., a ratio of more than 1:1.1, or more than about 1:5, if detectable.

Antibody fragments that retain an ability to selectively bind with the VEGF receptor are within the scope of the invention and include:

(1) Fab is the fragment of an antibody that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule that can be obtained by treating whole antibody with pepsin, followed by reduction, to yield an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region.

(3) (Fab')$_2$ is the fragment of an antibody that can be obtained by treating whole antibody with the enzyme pepsin without subsequent reduction. F(ab')$_2$ is a dimer of two Fab' fragments held together by two disulfide bonds.

(4) Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

(5) Single chain antibody ("SCA"), defined as a genetically engineered molecule containing the variable region of the light chain ($V_L$), the variable region of the heavy chain ($V_H$), linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the $V_H$ and $V_L$ domains that enables the sFv to form the desired structure for antigen binding. For a review of sFv fragments, see Pluckthun in The Pharmacology of Monoclonal Antibodies, vol. 113, Rosenburg and Moore eds. Springer-Verlag, N.Y., pp. 269 315 (1994).

If desired, the antibodies produced by the B cells can be modified in any suitable process. For example, the binding affinity of the antibodies can be increased via various methods known in the art. For example, binding characteristics can be improved by direct mutation, methods of affinity maturation, phage display, or chain shuffling within the nucleic acids encoding the antibody molecules. For example, individual residues or combinations of residues can be randomized so that in a population of otherwise identical antigen binding sites, all twenty amino acids are found at particular positions. Binding characteristics can also be improved by methods of affinity maturation. (See, e.g., Yang et al. (1995) *J. Mol.* 254, 392-403; Hawkins et al. (1992) *J. Mol. Bio.* 226, 889-896; or Low et al. (1996) *J. Mol. Bio.* 250, 359-368 (each of which is hereby incorporated by reference in its entirety, particularly with respect to methods of increasing the binding affinity of antibodies)). Methods known in the art include for example, Marks et al. *Bio/Technology*, 10:779-783 (1992) describes affinity maturation by VH and VL domain shuffling; random mutagenesis of CDR and/or framework residues is described by Barbas et al. *Proc. Natl. Acad. Sci., USA* 91:3809-3813 (1994); Schier et al. *Gene,* 169:147-155 (1995); Yelton et al. *J. Immunol.,* 155:1994-2004 (1995); Jackson et al., *J. Immunol.,* 154(7):3310-3319 (1995); and Hawkins et al, *J. Mol. Biol.,* 226:889-896 (1992).

Strategies for antibody optimization are sometimes carried out using random mutagenesis. In these cases positions are chosen randomly, or amino acid changes are made using simplistic rules. For example all residues may be mutated to alanine, referred to as alanine scanning. WO 9523813 (which is hereby incorporated by reference in its entirety) teaches in vitro methods of increasing antibody affinities utilizing alanine scanning mutagenesis. Alanine scanning mutagenesis can also be used, for example, to map the antigen binding residues of an antibody (Kelley et al., 1993, *Biochemistry* 32:6828-6835; Vajdos et al., 2002, *J. Mol. Biol.* 320:415-428). Sequence-based methods of affinity maturation (see, U.S. Pat. Application No. 2003/022240 A1 and U.S. Pat. No. 2002/177170 A1, both hereby incorporated by reference in their entireties) may also be used to increase the binding affinities of antibodies.

Antibodies within the scope of the invention can be of any isotype, including IgG, IgA, IgE, IgD, and IgM. IgG isotype antibodies can be further subdivided into IgG1, IgG2, IgG3, and IgG4 subtypes. IgA antibodies can be further subdivided into IgA1 and IgA2 subtypes.

Modification of Amino Acid and/or Polynucleotide Sequences

Substitution of amino acids other than those specifically exemplified or naturally present in an antibody of the invention are also within the scope of the present invention. For example, non-natural amino acids can be substituted for the amino acids of the antibody, so long as the antibody having the substituted amino acids retains substantially the same functional activity as the antibody in which amino acids have not been substituted.

Examples of non-natural amino acids include, but are not limited to, ornithine, citrulline, hydroxyproline, homoserine, phenylglycine, taurine, iodotyrosine, 2,4-diaminobutyric acid, a-amino isobutyric acid, 4-aminobutyric acid, 2-amino butyric acid, γ-amino butyric acid, e-amino hexanoic acid, 6-amino hexanoic acid, 2-amino isobutyric acid, 3-amino propionic acid, norleucine, norvaline, sarcosine, homocitrulline, cysteic acid, t-butylglycine, t-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) foam or L (levorotary) form.

Amino acids can be generally categorized in the following classes: non-polar, uncharged polar, basic, and acidic. Conservative substitutions whereby a modified antibody of the present invention having an amino acid of one class is replaced with another amino acid of the same class fall within the scope of the subject invention so long as the modified antibody having the substitution still retains substantially the same functional activity (e.g., the ability to bind to the VEGF receptor) as the antibody that does not have the substitution. Polynucleotides encoding a modified antibody having one or more amino acid substitutions in the sequence are also within the scope of the present invention. Table 1 below provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

The subject invention also concerns variants of the polynucleotides of the present invention that encode functional antibodies of the invention. Variant sequences include those sequences wherein one or more nucleotides of the sequence have been substituted, deleted, and/or inserted.

The nucleotides that can be substituted for natural nucleotides of DNA have a base moiety that can include, but is not limited to, inosine, 5-fluorouracil, 5-bromouracil, hypoxanthine, 1-methylguanine, 5-methylcytosine, and tritylated bases. The sugar moiety of the nucleotide in a sequence can also be modified and includes, but is not limited to, arabinose, xylulose, and hexose. In addition, the adenine, cytosine, guanine, thymine, and uracil bases of the nucleotides can be modified with acetyl, methyl, and/or thio groups. Sequences containing nucleotide substitutions, deletions, and/or insertions can be prepared and tested using standard techniques known in the art.

Fragments and variants of an antibody of the present invention can be generated as described herein and tested for the presence of the desired binding characteristics using standard techniques known in the art. Thus, an ordinarily skilled artisan can readily prepare and test fragments and variants of the antibody of the invention and determine whether the antibody retains functional activity relative to the full-length or a non-variant antibody.

Polynucleotides and polypeptides within the scope of the subject invention can also be defined in terms of more particular identity and/or similarity ranges with those sequences of the invention specifically exemplified herein. The sequence identity will typically be greater than 60%, preferably greater than 75%, more preferably greater than 80%, even more preferably greater than 90%, and can be greater than 95%. The identity and/or similarity of a sequence can be 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein.

Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCBI/NIH website.

The subject invention also contemplates those polynucleotide molecules having sequences which are sufficiently homologous with the polynucleotide sequences exemplified herein so as to permit hybridization with that sequence under standard stringent conditions and standard methods (Maniatis et al., 1982). As used herein, "stringent" conditions for hybridization refers to conditions wherein hybridization is typically carried out overnight at 20-25 C below the melting temperature (Tm) of the DNA hybrid in 6×SSPE, 5×Denhardt's solution, 0.1% SDS, 0.1 mg/ml denatured DNA. The melting temperature, Tm, is described by the following formula (Beltz et al., 1983):

$$Tm = 81.5\ C + 16.6\ \text{Log}\ [Na+] + 0.41(\%\ G+C) - 0.61(\%\ \text{formamide}) - 600/\text{length of duplex in base pairs}.$$

Washes are typically carried out as follows:
(1) Twice at room temperature for 15 minutes in 1×SSPE, 0.1% SDS (low stringency wash).
(2) Once at Tm-20 C for 15 minutes in 0.2×SSPE, 0.1% SDS (moderate stringency wash).

Expression Constructs

As used herein, the term "expression construct" refers to a combination of nucleic acid sequences that provides for transcription of an operably linked nucleic acid sequence. As used herein, the term "operably linked" refers to a juxtaposition of the components described wherein the components are in a relationship that permits them to function in their intended manner. In general, operably linked components are in contiguous relation.

Expression constructs of the invention will also generally include regulatory elements that are functional in the intended host cell in which the expression construct is to be expressed. Thus, a person of ordinary skill in the art can select regulatory elements for use in, for example, bacterial host cells, yeast host cells, plant host cells, insect host cells, mammalian host cells, and human host cells. Regulatory elements include promoters, transcription termination sequences, translation termination sequences, enhancers, and polyadenylation elements.

An expression construct of the invention can comprise a promoter sequence operably linked to a polynucleotide sequence encoding a peptide of the invention. Promoters can be incorporated into a polynucleotide using standard techniques known in the art. Multiple copies of promoters or multiple promoters can be used in an expression construct of the invention. In a preferred embodiment, a promoter can be positioned about the same distance from the transcription start site as it is from the transcription start site in its natural genetic environment. Some variation in this distance is permitted without substantial decrease in promoter activity. A transcription start site is typically included in the expression construct.

For expression in animal cells, an expression construct of the invention can comprise suitable promoters that can drive transcription of the polynucleotide sequence. If the cells are mammalian cells, then promoters such as, for example, actin promoter, metallothionein promoter, NF-kappaB promoter, EGR promoter, SRE promoter, IL-2 promoter, NFAT promoter, osteocalcin promoter, SV40 early promoter and SV40 late promoter, Lck promoter, BMP5 promoter, TRP-1 promoter, murine mammary tumor virus long terminal repeat promoter, STAT promoter, or an immunoglobulin promoter can be used in the expression construct. The baculovirus polyhedrin promoter can be used with an expression construct of the invention for expression in insect cells. Promoters suitable for use with an expression construct of the invention in yeast cells include, but are not limited to, 3-phosphoglycerate kinase promoter, glyceraldehyde-3-phosphate dehydrogenase promoter, metallothionein promoter, alcohol dehydrogenase-2 promoter, and hexokinase promoter.

Expression constructs of the invention may optionally contain a transcription termination sequence, a translation termination sequence, signal peptide sequence, and/or enhancer elements. Transcription termination regions can typically be obtained from the 3' untranslated region of a eukaryotic or viral gene sequence. Transcription termination sequences can be positioned downstream of a coding sequence to provide for efficient termination. Signal peptides are a group of short amino terminal sequences that encode information responsible for the relocation of an operably linked peptide to a wide range of post-translational cellular destinations, ranging from a specific organelle compartment to sites of protein action and the extracellular environment. Targeting a peptide to an intended cellular and/or extracellular destination through the use of operably linked signal peptide sequence is contemplated for use with the peptides of the invention. Chemical enhancers are cis-acting elements that increase gene transcription and can also be included in the expression construct. Chemical enhancer elements are known in the art, and include, but are not limited to, the CaMV 35S enhancer element, cytomegalovirus (CMV) early promoter enhancer element, and the SV40 enhancer element. DNA sequences which direct polyadenylation of the mRNA encoded by the structural gene can also be included in the expression construct.

Unique restriction enzyme sites can be included at the 5' and 3' ends of the expression construct to allow for insertion into a polynucleotide vector. As used herein, the term "vector" refers to any genetic element, including for example, plasmids, cosmids, chromosomes, phage, virus, and the like, which is capable of replication when associated with proper control elements and which can transfer polynucleotide sequences between cells. Vectors contain a nucleotide sequence that permits the vector to replicate in a selected host cell. A number of vectors are available for expression and/or cloning, and include, but are not limited to, pBR322, pUC series, M13 series, and pBLUESCRIPT vectors (Stratagene, La Jolla, Calif.).

Transformation of Cells

Polynucleotides, vectors, and expression constructs of the subject invention can be introduced into a cell by methods known in the art. Such methods include transfection, microinjection, electroporation, lipofection, cell fusion, calcium phosphate precipitation, and by biolistic methods. In one embodiment, a polynucleotide or expression construct of the invention can be introduced in vivo via a viral vector such as adeno-associated virus (AAV), herpes simplex virus (HSV), papillomavirus, adenovirus, and Epstein-Barr virus (EBV). Attenuated or defective forms of viral vectors that can be used with the subject invention are known in the art. Typically, defective virus is not capable of infection after the virus is introduced into a cell. Polynucleotides, vectors, and expression constructs of the invention can also be introduced in vivo via lipofection (DNA transfection via liposomes prepared from synthetic cationic lipids) (Felgner et al., 1987). Synthetic cationic lipids (LIPOFECTIN, Invitrogen Corp., La Jolla, Calif.) can be used to prepare liposomes to encapsulate a polynucleotide, vector, or expression construct of the invention. A polynucleotide, vector, or expression construct of the invention can also be introduced in vivo as naked DNA using methods known in the art, such as transfection, microinjection, electroporation, calcium phosphate precipitation, and by biolistic methods.

Treatment of Pathological Angiogenesis

The invention provides for a method for the inhibition of angiogenesis in a tissue, and thereby inhibiting events in the tissue which depend upon angiogenesis. Generally, the method comprises administering to the tissue a composition comprising an angiogenesis-inhibiting amount of an antibody of the subject invention.

As described earlier, angiogenesis includes a variety of processes involving neovascularization of a tissue including "sprouting", vasculogenesis, or vessel enlargement, all of which angiogenesis processes involve disruption of extracellular matrix collagen in blood vessels. With the exception of traumatic wound healing, corpus leuteum formation and embryogenesis, it is believed that the majority of angiogenesis processes are associated with disease processes and therefore the use of the present therapeutic methods are selective for the disease.

There are a variety of diseases in which angiogenesis is believed to be important, referred to as angiogenic diseases, including but not limited to, inflammatory disorders such as immune and non-immune inflammation, chronic articular rheumatism and psoriasis, disorders associated with inappropriate or inopportune invasion of vessels such as diabetic retinopathy, neovascular glaucoma, restenosis, capillary proliferation in atherosclerotic plaques and osteoporosis, and cancer associated disorders, such as solid tumors, solid tumor metastases, angiofibromas, retrolental fibroplasia, hemangiomas, Kaposi's sarcoma and the like cancers which require neovascularization to support tumor growth. Other suitable tumors include melanoma, carcinoma, sarcoma, fibrosarcoma, glioma and astrocytoma.

Thus, methods which inhibit angiogenesis in a diseased tissue ameliorate symptoms of the disease and, depending upon the disease, can contribute to cure of the disease. In one embodiment, the invention contemplates inhibition of angiogenesis, per se, in a tissue.

As described herein, any of a variety of tissues, or organs comprised of organized tissues, can support angiogenesis in disease conditions including skin, muscle, gut, connective tissue, joints, bones and the like tissue in which blood vessels can invade upon angiogenic stimuli. Tissue, as used herein, also encompasses all bodily fluids, secretions and the like, such as serum, blood, cerebrospinal fluid, plasma, urine, synovial fluid, vitreous humor.

Thus, in one related embodiment, a tissue to be treated is an inflamed tissue and the angiogenesis to be inhibited is inflamed tissue angiogenesis where there is neovascularization of inflamed tissue. In this class the method contemplates inhibition of angiogenesis in arthritic tissues, such as in a patient with chronic articular rheumatism, in immune or non-immune inflamed tissues, in psoriatic tissue and the like.

The patient treated in the present invention in its many embodiments is desirably a human patient, although it is to be understood that the principles of the invention indicate that the invention is effective with respect to all mammals, which are intended to be included in the term "patient". In this context, a mammal is understood to include any mammalian species in which treatment of diseases associated with angiogenesis is desirable, particularly agricultural and domestic mammalian species. Such a patient can be, for example, a pig, a cow, a horse, a goat, a sheep, a mule, a donkey, a dog, a cat, a rabbit, a mouse and a rat.

In another related embodiment, a tissue to be treated is a retinal tissue of a patient with diabetic retinopathy, macular degeneration or neovascular glaucoma and the angiogenesis to be inhibited is retinal tissue angiogenesis where there is neovascularization of retinal tissue.

In an additional related embodiment, a tissue to be treated is a tumor tissue of a patient with a solid tumor, a metastasis, a skin cancer, a breast cancer, a hemangioma or angiofibroma and the like cancer, and the angiogenesis to be inhibited is tumor tissue angiogenesis where there is neovascularization of a tumor tissue. Typical solid tumor tissues treatable by the present methods include lung, pancreas, breast, colon, laryngeal, ovarian, Kaposi's Sarcoma and the like tissues. Exemplary tumor tissue angiogenesis, and inhibition thereof, is described in the Examples. In addition, liquid tumor, such as leukemia may also be treated with anti-VEGFR2 antibody described in this invention. Leukemia may also rely on angiogenesis to support cell growth, particularly in bone marrow. In these situations, anti-VEGFR2 may provide an effective means for treatment.

Inhibition of tumor tissue angiogenesis is a particularly preferred embodiment because of the important role neovascularization plays in tumor growth. In the absence of neovascularization of tumor tissue, the tumor tissue does not obtain the required nutrients, slows in growth, ceases additional growth, regresses and ultimately becomes necrotic resulting in killing of the tumor.

Stated in other words, the present invention provides for a method of inhibiting tumor neovascularization by inhibiting tumor angiogenesis. Similarly, the invention provides a method of inhibiting tumor growth by practicing the angiogenesis-inhibiting methods.

By their ability to inhibit neovascularization, the methods of the invention also are effective against the formation of metastases because (1) their formation requires vascularization of a primary tumor so that the metastatic cancer cells can exit the primary tumor and (2) their establishment in a secondary site requires neovascularization to support growth of the metastases.

In a related embodiment, the invention contemplates the practice of the method in conjunction with other therapies such as conventional chemotherapy directed against solid tumors and for control of establishment of metastases. The administration of angiogenesis inhibitor is typically conducted during or after chemotherapy, although it is preferable to inhibit angiogenesis after a regimen of chemotherapy at times where the tumor tissue will be responding to the toxic assault by inducing angiogenesis to recover by the provision of a blood supply and nutrients to the tumor tissue. In addition, it is preferred to administer the angiogenesis inhibition methods after surgery where solid tumors have been removed as a prophylaxis against metastases.

Insofar as the present methods apply to inhibition of tumor neovascularization, the methods also can apply to regression of established tumors.

Restenosis is a process of smooth muscle cell (SMC) migration and proliferation at the site of percutaneous transluminal coronary angioplasty which hampers the success of angioplasty. The migration and proliferation of SMCs associated with blood vessels during restenosis is related to the process of angiogenesis which is inhibited by the present methods. Therefore, the invention also contemplates inhibition of restenosis by inhibiting angiogenic related processes according to the present methods in a patient following angioplasty procedures. For inhibition of restenosis, the antibody of the invention is typically administered after the angioplasty procedure for from about 2 to about 28 days, and more typically for about the first 14 days following the procedure.

The present method for inhibiting angiogenesis in a tissue, and therefore for also practicing the methods for treatment of angiogenesis-related diseases, comprises contacting a tissue in which angiogenesis is occurring, or is at risk for occurring, with a therapeutic composition comprising a therapeutically effective amount of an antibody of the subject invention. Thus, the method comprises administering to a patient a therapeutically effective amount of a physiologically tolerable composition containing an antibody of the invention.

The dosage ranges for the administration of the antibody depend upon the form of the antibody, and its potency, as described further herein, and are amounts large enough to produce the desired effect in which angiogenesis and the disease symptoms mediated by angiogenesis are ameliorated. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art. The dosage also can be adjusted by the individual physician in the event of any complication.

Routes of Administration

The antibodies of the invention can be administered parenterally by injection or by gradual infusion over time. Although the tissue to be treated can typically be accessed in the body by systemic administration and therefore most often treated by intravenous administration of therapeutic compositions, other tissues and delivery means are contemplated where there is a likelihood that the tissue targeted contains the target molecule. Thus, antibodies, and derivatives thereof can be administered intravenously, intraperitoneally, intramuscularly, subcutaneously, intracavity, transdermally, topically, intraocularly, orally, intranasally and can be delivered by peristaltic means.

The therapeutic compositions containing an antibody of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered and timing depends on the patient to be treated, capacity of the patient's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for administration also are variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

The antibody can be administered intravenously, transdermally, intrasynovially, intramuscularly, intratumorally, intraocularly, intranasally, intrathecally, topically or orally. Further, the antibody may be administered in conjunction with chemotherapy or in conjunction with radiation. This method is used when the tissue is inflamed and angiogenesis is occurring, when the tissue is present in a mammal, or when the tissue is arthritic, ocular, retinal or a hemangioma.

This method would be applicable when the tumor or metastasis is a melanoma, carcinoma, sarcoma, fibrosarcoma, glioma or in another embodiment, the invention is a method of inhibiting psoriasis, macular degeneration, or restenosis in a tissue.

Where the growth of new blood vessels is the cause of, or contributes to, the pathology associated with a disease, inhibition of angiogenesis will reduce the deleterious effects of the disease. Examples include psoriasis, rheumatoid arthritis, diabetic retinopathy, inflammatory diseases, restenosis, macular degeneration and the like. Where the growth of new blood vessels is required to support growth of a deleterious tissue, inhibition of angiogenesis will reduce the blood supply to the tissue and thereby contribute to reduction in tissue mass based on blood supply requirements. Examples include growth of tumors where neovascularization is a continual requirement in order that the tumor grows beyond a few millimeters in thickness, and for the establishment of solid tumor metastases.

The methods of the present invention are effective in part because the therapy is highly selective for angiogenesis and not other biological processes.

Moreover, the antibodies of the invention are highly potent suggesting that they may have therapeutic benefits at low concentrations.

Therapeutic Compositions

The present invention contemplates therapeutic compositions useful for practicing the therapeutic methods described herein. Therapeutic compositions of the present invention contain a physiologically tolerable carrier together with a therapeutically effective amount of an antibody as described herein, dissolved or dispersed therein as an active ingredient. In a preferred embodiment, the therapeutic composition is not immunogenic or has reduced immunogenicity when administered to a mammal or human patient for therapeutic purposes.

A therapeutically effective amount is an amount of an antibody of the invention sufficient to produce a measurable inhibition of angiogenesis in the tissue being treated, i.e., an angiogenesis-inhibiting amount. Inhibition of angiogenesis can be measured in situ by immunohistochemistry, or by other methods known to one skilled in the art.

Potency of an antagonist of the invention can be measured by a variety of means including inhibition of angiogenesis in the CAM assay, in an in vivo rabbit eye assay, and in a in vivo chimeric mouse:human assay.

A therapeutically effective amount of an antagonist of this invention in the form of a monoclonal antibody is typically an amount such that when administered in a physiologically tolerable composition is sufficient to achieve a plasma concentration of from about 0.01 microgram (ug) per milliliter (mL) to about 100 ug/mL, preferably from about 1 ug/mL to about 5 ug/mL, and usually about 5 ug/mL. Stated differently, the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily, for one or several days.

Where the antagonist is in the form of a fragment of a monoclonal antibody, the amount can readily be adjusted based on the mass of the fragment relative to the mass of the whole antibody. A preferred plasma concentration in molarity is from about 2 micromolar (uM) to about 5 millimolar (mM) and preferably about 100 uM to 1 mM antibody antagonist.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal.

The preparation of a pharmacological composition that contains active ingredients dissolved or dispersed therein is well understood in the art and need not be limited based on formulation. Typically such compositions are prepared as injectables either as liquid solutions or suspensions; however, solid forms suitable for solution, or suspensions, in liquid prior to use also can be prepared. The preparation also can be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of a polypeptide) that are formed with inorganic acids such as, for example, hydrochloric or phosphoric acids, or such organic acids as acetic, tartaric, mandelic and the like. Salts formed with the free carboxyl groups also can be derived from inorganic bases such as, for example, sodium, potassium, ammonium, calcium or ferric hydroxides, and such organic bases as isopropylamine, trimethylamine, 2-ethylamino ethanol, histidine, procaine and the like. Particularly preferred are the salts of TFA and HCl.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions also can contain liquid phases in addition to and to the exclusion of water. Exemplary of such additional liquid phases are glycerin, vegetable oils such as cottonseed oil, and water-oil emulsions.

A therapeutic composition contains an angiogenesis-inhibiting amount of an antagonist of the present invention, typically formulated to contain an amount of at least 0.01 weight percent of antagonist per weight of total therapeutic composition. A weight percent is a ratio by weight of inhibitor to total composition. Thus, for example, 0.01 weight percent is 0.01 grams of inhibitor per 100 grams of total composition.

An antibody can be conjugated with cytotoxins, cytotoxic agents, for delivery to a to tumor or other tissue undergoing angiogenesis. Such conjugates can be made with a cytolysin or an exotoxin, for example ricin A, diphtheria toxin A, or Pseudomonas exotoxin and fragments thereof. The cytotoxic agent can also be radioactively labeled with an isotope so as to locally deliver a toxic dose of radioactivity to an angiogenic tissue.

Antibodies of the invention can also be used to deliver an enzyme to a target wherein the enzyme is capable of converting a prodrug into an active form of the drug for use in, for example, antibody-directed enzyme activated prodrug therapy (ADEPT) (see, e.g., Syrigos, K. N. (1999) Anticancer Res. 19:605-13). Briefly, an antagonist of the invention is conjugated with an enzyme, such as a lactamase, protease or esterase, that can convert a non-toxic or inactive prodrug into a toxic or active drug. Because the antibody of the invention localizes to sites of angiogenesis, and particularly to sites of tumors or metastases, toxic drugs can be directed to such sites Detection Methods Antibodies of the invention also are suitable for detection of angiogenesis in tissues. For example, the antibody can be used in immunohistochemical techniques to stain tissues ex vivo. Immunological techniques such as immunostaining and ELISA are described in, for example, Receptor Binding Techniques Methods in Molecular Biology. 106. ed. M. Keen. Humana Press, 1999; Brooks et al. (1998) Cell 92:391-400; Brooks et al. (1996) Cell 85:683-693; and Brooks et al. (1993) J. Cell. Biol. 122:1351-1359.

The antibody once bound to the target tissue can be detected either directly or indirectly. Direct detection can be performed on antagonists that comprise a detectable label such as a fluorochrome, a radioactive tag, paramagnetic heavy metal or diagnostic dye.

Alternatively, detection can occur through a secondary interaction. For example, a detectably labeled antibody that recognizes the antagonist can be used to visualize the location of the antagonist. For example, if the antagonist is a monoclonal antibody of mouse origin, a goat anti-mouse antibody that is suitably labeled can be used. One of skill in the art can determine suitable secondary antibodies for use with various antagonists.

For in vivo detection, it is preferable to use a detectably labeled antibody. The labeled antibody is administered to a patient intravenously, intramuscularly, etc. Labels suitable for detection within a patient are particularly preferred. For example, paramagnetically labeled antibodies can be detected by magnetic resonance imaging. Radioactively tagged antibodies also can be detected.

EXAMPLES

This invention was further demonstrated through the following examples. It should be understood that the scope of this invention is not limited to the examples. Furthermore, those with skill in the art may modify or alter this invention after reading this disclosure; these modified variants should be regarded as equivalent to embodiments and fall into the scope of this invention.

The following examples, if not described in detail, use techniques commonly known to those with skill in the art and may follow the experimental protocols or conditions described by references such as Molecular Cloning, A Laboratory Manual (Sambrook, et al., Cold Spring Harbor Laboratory Press) or Antibodies: A Laboratory Manual, (Ed Harlow and David Lane, Cold Spring Harbor Laboratory Press), etc., or based on manufacture's instruction.

All patents, patent applications, provisional applications, and publications referred to or cited herein are incorporated by reference in their entirety, including all figures and tables, to the extent they are not inconsistent with the explicit teachings of this specification.

Following are examples, which illustrate procedures for practicing the invention. These examples should not be construed as limiting. All percentages are by weight and all solvent mixture proportions are by volume unless otherwise noted.

Example 1

Preparation of Human Anti-VEGFR2 Antibody

To generate fully human anti-VEGFR antibody, human serum samples were screened by ELISA to identify patients who are positive for anti-VEGFR2.

In this ELISA assay, 96-well plates were coated with human recombinant VEGFR2 and blocked with 2% bovine albumin. Diluted human serum was added to each well and then detected by HRP-conjugated goat anti-human IgG. After incubation with HRP substrate, the ELISA plates were read in a micro-plate reader.

Using this method, a sample with anti-VEGFR2 positive ELISA was identified. The peripheral blood was collected from this person and the peripheral blood mononuclear cells (PBMC) were isolated using Ficoll gradient density centrifugation. SCID mice were transplanted with the PBMC and then immunized multiple times with human recombinant VEGFR2 protein.

The anti-VEGFR2 antibody titers in mouse sera were determined by the ELISA assay. After high serum anti-VEGFR2 antibody titer was reached, spleens were dissected and splenocytes isolated to fuse with myeloma cells to generate hybridoma cells. The fused hybridomas were grown in selection medium to generate hybridoma clones.

Example 2

Effective Binding of the Anti-VEGFR2 Antibody to VEGFR2

The hybridoma cell clones were grown in 96-well plates in RPMI-1640 complete medium. Supernatants were collected from each hybridoma clone and assayed for specific antibodies using ELISA. In this assay, ELISA plates were coated with soluble recombinant human VEGFR2 and blocked with 2% BSA. Then hybridoma supernatants were properly diluted and added to each well, followed by HRP-conjugated goat anti-human IgG. The plates were then incubated with HRP substrate and OD values read at a wavelength of 650 nm using a micro-plate reader.

A number of hybridoma clones that secrete anti-VEGFR2 antibodies were identified. The hybridoma clones that secrete specific antibodies against VEGFR2 were expanded to 6-well plates, and then T-175 flasks. Supernatants were harvested from the flasks. Isotypes of the antibodies secreted from hybridoma clones were determined using an IgG isotyping kit and concentrations of antibodies in the supernatants were measured by an ELISA assay using the corresponding antibody subtypes as a standard. Antibody concentrations in the hybridoma supernatants were normalized and diluted.

These antibody supernatants were used to compare relative binding affinities of antibodies to VEGFR2 by an ELISA assay. By this approach, several monoclonal antibody clones that show high affinity to VEGFR2 were identified.

Example 3

Blocking VEGFR2 and VEGF Binding by Anti-VEGFR2 Monoclonal Antibodies

After the hybridoma clones expressing anti-VEGFR2 antibodies were identified in the initial screening, the ability of these antibodies to block VEGF-VEGFR2 binding were examined.

In this secondary screening assay, 96-well ELISA plates were coated with human recombinant VEGF and blocked with BSA. In a separate 96-well plate, anti-VEGFR2 antibodies at various concentrations were mixed with recombinant human VEGFR2. The mixtures were incubated at 37° C. for one hour and then transferred to the ELISA plate that was blocked with BSA. After rinse, HRP-conjugated goat anti-human IgG was added to each well, followed by HRP substrate and OD reading at 650 nm in a micro-plate reader.

By this methodology, a monoclonal antibody clone, designated as AC88, that is capable of completely blocking VEGF-VEGFR2 binding was identified. AC88 was confirmed as human IgG1 by antibody isotyping.

Example 4

The Anti-VEGFR2 Antibody can Completely Block VEGF-Induced HUVEC Proliferation

In order to demonstrate anti-angiogenic effects of this anti-VEGFR2 antibody, the antibody was evaluated in a vascular endothelial cell proliferation assay.

Human umbilical vein endothelial cell proliferation assay is one of the most widely used in vitro model in angiogenesis research. HUVEC cells express VEGFR2 and undergo cell proliferation in response to VEGF stimulation. Therefore, HUVEC cells can be used to evaluate neutralization activity of the anti-VEGFR2 antibody.

In this assay, HUVEC cells were seeded into 24-well plates. After 24 hours, cells were fed with basal medium supplemented with 10 ng/ml VEGF. AC88 antibody was added to wells at various concentrations (0.1-5 µg/ml) and the plates were cultured at 37 C in a 10% CO2 incubator. After 48 hours, cells were digested by trypsin and cell numbers were counted. In control wells, normal IgG at various concentrations were added.

Results showed that in the wells that contain 1 µg/ml of anti-VEGFR2 antibody, HUVEC proliferation was completely inhibited. In contrast, in the control wells in which the same amount (1 µg/ml) of normal antibody was added, no inhibitory effect on HUVEC proliferation was observed.

Hence, the anti-VEGFR2 antibody of the subject invention can completely inhibit vascular endothelial cell proliferation; thus this antibody is capable of blocking angiogenesis. In a further study, it was shown that the AC88 antibody does not bind to mouse VEGFR2. Therefore, it is not suitable to assess the biological activity of this antibody in regular mouse in vivo models.

Example 5

Molecular Cloning of the Anti-VEGFR2 Antibody and Expression of the Recombinant Antibody in Cell Culture System Hybridoma cells are not suitable for large-scale industrial production of monoclonal antibodies. In order to express recombinant antibody, DNA sequences of the AC88 antibody were cloned by molecular cloning.

DNA sequences of the antibody heavy and light chain variable regions were identified by using Rapid Amplification of cDNA Ends (RACE). Briefly, AC88 hybridoma cells were harvested from culture and total RNA was isolated using a total RNA isolation kit (Promega), followed by cDNA synthesis using reverse transcriptase (BD Biosciences). Antibody heavy and light chain sequences were amplified from AC88 cDNA by PCR reaction using RACE cDNA amplification kit (BD Biosciences). The forward PCR primer was from the kit; the reverse PCR primers were designed based on the C-terminus of human IgG1 heavy chain (SEQ ID NO:3) or kappa light chain (SEQ ID NO:4) sequences. PCR parameters were set up according to kit instruction.

PCR products were verified in 1% agarose gel and cloned into a TA cloning vector (Invitrogen). The clones with correct inserts were confirmed by restriction endonuclease digestion. The inserts were analyzed by DNA sequencing by which the DNA sequences of the AC88 antibody heavy and light chains were revealed. Further amino acid sequence analyses showed that the heavy chain sequence of the antibody contained a IgG variable region and constant region, and the light chain sequence contained the kappa light chain variable region and constant region. The AC88 heavy chain constant region is identical to typical human IgG1 sequence.

The verified antibody heavy and light DNA fragments were digested with restriction enzymes and inserted into mammalian expression plasmid pCDNA 3.1. The pCDNA 3.1 plasmids containing antibody heavy or light chains were purified and co-transfected into CHO cells using lipofectamine transfection kit (Invitrogen). After 48-72 hours, antibody concentrations in the supernatants were measured by ELISA assay. By this method, recombinant AC88 antibody was expressed from plasmids, demonstrating that AC88 can be produced by genetic engineering technology.

Example 6

Establishment of Expression Cell Lines that Produce Anti-VEGFR2 Antibody in High Levels To express the AC88 monoclonal antibody with high efficiency, a stably transfected CHO cell line for the AC88 antibody was generated, followed by gene amplification to yield CHO cell clones with high expression levels. The AC88 heavy and light chain sequences were first cloned into an expression plasmid that encodes DHFR. In this plasmid, the heavy and light chains are located in the same vector and controlled by separate CMV promoters. The DHFR gene was driven by a SV40 early enhancer.

The plasmids encoding the AC88 heavy or light chain were purified using plasmid Maxi preparation kit (Qiagen) and transfected into DHFR-deficient CHO cells (ATCC) by electroporation. In three days post-transfection, CHO cells were trypsinized, diluted, and plated in selection medium.

After three weeks, single colonies were picked and transferred into 96-well plates for evaluation of antibody expression levels by ELISA. High antibody production clones were transferred to 6-well plates. Once cells reached confluence, supernatants were collected to determine antibody concentrations by ELISA and cell numbers were counted to calculate specific antibody productivities. The clones with highest antibody expression levels were seeded in 10-cm dishes and subjected to increased methotrexate (MTX) pressures, with final MTX concentration at 500-2000 nM. After gene amplification, the best clones with highest specific antibody productivity were chosen.

Using this procedure, a number of high antibody production CHO clones were obtained with specific antibody productivity over 30 pg/cell/day. Furthermore, these clones are stable and can be used for large-scale production of this monoclonal antibody.

Example 7

Purification of the Anti-VEGFR2 Antibody

The AC88 monoclonal antibody can be purified using protein A affinity chromatography as a initial step.

The cell culture supernatants of AC88 CHO cell clone were collected and filtrated through 0.45 µm membrane. Protein A resin (GE) was prepared and packed into a suitable column according to the manufacturer's instruction. The filtrated antibody supernatants were passed through the protein A chromatography column at a proper flow rate and washed with PBS. The antibody was eluted from a column by low pH Glysine-HCl buffer. In reducing condition, the purified antibody appeared as two distinct bands, at the apparent molecular weights approximately 55 and 22 kD respectively, consistent with the molecular weights of antibody heavy and light chains. Hence, protein A can be used to efficiently purify AC88 antibody.

From this basis, antibody with higher purity can be achieved in combination with other chromatography methods. Protein concentrations of purified antibody were determined by Bradford assay. The purified antibody can be properly formulated in a suitable concentration and developed as a mAb therapeutic.

It should be understood that the examples and embodiments described herein are for illustrative purposes only and that various modifications or changes in light thereof will be suggested to persons skilled in the art and are to be included within the spirit and purview of this application.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way, Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents, The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

We claim:

1. An isolated monoclonal antibody that binds to human Vascular Endothelial Growth Factor Receptor 2 (VEGFR2), comprising an immunoglobulin heavy chain and an immunoglobulin light chain, wherein the variable region of said heavy chain comprises the variable region of SEQ ID No:1 and the variable region of said light chain comprises the variable region of SEQ ID NO:2.

2. An isolated monoclonal antibody that binds to human Vascular Endothelial Growth Factor Receptor 2 (VEGFR2), comprising an immunoglobulin heavy chain and an immunoglobulin light chain, wherein said heavy chain comprises SEQ ID No:1 and said light chain comprises SEQ ID NO:2.

3. A fusion construct comprising the monoclonal antibody according to claim 1.

4. The fusion construct, according to claim 3, wherein the fusion construct further comprises an entity selected from the group consisting of a linker, a toxin, a carrier, and/or a detectable molecule.

5. A fusion construct comprising the monoclonal antibody according to claim 2.

6. The fusion construct, according to claim 5, wherein the fusion construct further comprises an entity selected from the group consisting of a linker, a toxin, a carrier, and/or a detectable molecule.

* * * * *

SEQUENCE LISTING

```
<160> NUMBER OF SEQ ID NOS: 4

<210> SEQ ID NO 1
<211> LENGTH: 467
<212> TYPE: PRT
<213> ORGANISM: Artificial Sequence
<220> FEATURE:
<223> OTHER INFORMATION: Human Antibodies

<400> SEQUENCE: 1

Met Ser Val Ser Phe Leu Ile Phe Leu Pro Val Leu Gly Leu Pro Trp
1               5                   10                  15

Gly Val Leu Ser Glu Val Gln Leu Val Glu Ser Gly Gly Gly Leu Val
                20                  25                  30

Lys Pro Gly Gly Ser Leu Arg Leu Ser Cys Ala Ala Ser Gly Phe Thr
            35                  40                  45

Phe Ser Ser Tyr Ser Met Thr Trp Val Arg Gln Ala Pro Gly Lys Gly
        50                  55                  60

Leu Glu Trp Val Ser Ser Ile Ser Ser Ser Ser Ser Tyr Ile Tyr Tyr
65                  70                  75                  80

Ala Asp Ser Val Lys Gly Arg Phe Thr Ile Ser Arg Asp Asn Ala Lys
                85                  90                  95

Asn Ser Leu Tyr Leu Gln Met Asn Ser Leu Arg Ala Glu Asp Thr Ala
            100                 105                 110

Val Tyr Tyr Cys Ala Lys Ala Thr Ser Gly Tyr Met Asp Val Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255
```

-continued

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
                275                 280                 285

Glu Asp Pro Glu Val Lys Phe Asn Trp Tyr Val Asp Gly Val Glu Val
            290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
                355                 360                 365

Tyr Thr Leu Pro Pro Ser Arg Asp Glu Leu Thr Lys Asn Gln Val Ser
                370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
                435                 440                 445

His Glu Ala Leu His Asn His Tyr Thr Gln Lys Ser Leu Ser Leu Ser
                450                 455                 460

Pro Gly Lys
465

<210> SEQ ID NO 2
<211> LENGTH: 236
<212> TYPE: PRT
<213> ORGANISM: Artificial Sequence
<220> FEATURE:
<223> OTHER INFORMATION: Human Antibodies

<400> SEQUENCE: 2

Met Asp Met Arg Leu Pro Ala Gln Leu Gly Leu Leu Leu Leu Trp
1               5                   10                  15

Leu Pro Gly Ala Arg Cys Asp Ile Gln Met Thr Gln Ser Pro Ser Ser
                20                  25                  30

Leu Ser Ala Ser Val Gly Asp Arg Val Thr Ile Thr Cys Gln Ala Ser
            35                  40                  45

Gln Asp Ile Asn Asn Tyr Leu Asn Trp Tyr Gln Gln Lys Pro Gly Lys
        50                  55                  60

Ala Pro Lys Leu Leu Ile Tyr Asp Ala Ser Asn Leu Glu Thr Gly Val
65                  70                  75                  80

Pro Ser Arg Phe Ser Gly Ser Gly Ser Gly Thr Asp Phe Thr Leu Thr
                85                  90                  95

Ile Ser Ser Leu Glu Ser Glu Asp Ile Ala Thr Tyr Tyr Cys Gln Gln
                100                 105                 110

His Val Asn Tyr Pro Leu Thr Phe Gly Gly Gly Thr Lys Val Glu Ile
                115                 120                 125

Lys Arg Thr Val Ala Ala Pro Ser Val Phe Ile Phe Pro Pro Ser Asp
                130                 135                 140

Glu Gln Leu Lys Ser Gly Thr Ala Ser Val Val Cys Leu Leu Asn Asn

```
                145                 150                 155                 160
            Phe Tyr Pro Arg Glu Ala Lys Val Gln Trp Lys Val Asp Asn Ala Leu
                            165                 170                 175

Gln Ser Gly Asn Ser Gln Glu Ser Val Thr Glu Gln Asp Ser Lys Asp
                        180                 185                 190

Ser Thr Tyr Ser Leu Ser Ser Thr Leu Thr Leu Ser Lys Ala Asp Tyr
                    195                 200                 205

Glu Lys His Lys Val Tyr Ala Cys Glu Val Thr His Gln Gly Leu Ser
                        210                 215                 220

Ser Pro Val Thr Lys Ser Phe Asn Arg Gly Glu Cys
            225                 230                 235

<210> SEQ ID NO 3
<211> LENGTH: 20
<212> TYPE: DNA
<213> ORGANISM: Artificial Sequence
<220> FEATURE:
<223> OTHER INFORMATION: Synthesized - DNA Primers

<400> SEQUENCE: 3
tcttttaccc ggagacaggg                                                   20

<210> SEQ ID NO 4
<211> LENGTH: 23
<212> TYPE: DNA
<213> ORGANISM: Artificial Sequence
<220> FEATURE:
<223> OTHER INFORMATION: Synthesized - DNA Primers

<400> SEQUENCE: 4
ctaacactct cccctgttga agc                                               23
```